(12) United States Patent
Kazemizadeh et al.

(10) Patent No.: US 9,034,965 B2
(45) Date of Patent: May 19, 2015

(54) EPOXIDIZED COMPOSITION AND METHODS FOR MAKING THE SAME

(75) Inventors: Mohammad R. Kazemizadeh, Blooming Prairie, MN (US); Timothy E. McKinney, Cypress, TX (US); David E. Maixner, Blooming Prairie, MN (US); Zuzanna Donnelly, Wayne, PA (US)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 13/813,185

(22) PCT Filed: Aug. 5, 2011

(86) PCT No.: PCT/US2011/046697
§ 371 (c)(1),
(2), (4) Date: Feb. 12, 2013

(87) PCT Pub. No.: WO2012/019073
PCT Pub. Date: Feb. 9, 2012

(65) Prior Publication Data
US 2013/0203907 A1  Aug. 8, 2013

Related U.S. Application Data

(60) Provisional application No. 61/371,409, filed on Aug. 6, 2010.

(51) Int. Cl.
*C08K 5/10* (2006.01)
*C08K 5/15* (2006.01)
*C08K 5/1515* (2006.01)
*C08K 5/00* (2006.01)
*C08L 27/06* (2006.01)

(52) U.S. Cl.
CPC ............ *C08K 5/1515* (2013.01); *C08K 5/0016* (2013.01); *C08L 27/06* (2013.01)

(58) Field of Classification Search
USPC ........................................................ 524/318
See application file for complete search history.

(56) References Cited

U.S. PATENT DOCUMENTS

| 3,639,318 | A | 2/1972 | Tijunelis et al. |
| 4,670,494 | A | 6/1987 | Semenza, Jr. |
| 5,227,417 | A | 7/1993 | Kroushl, III |
| 8,557,139 | B2 * | 10/2013 | Eaton ...................... 252/182.28 |

FOREIGN PATENT DOCUMENTS

| WO | WO 2009/102877 A1 | 8/2009 |
| WO | WO 2010/006101 A2 | 1/2010 |

* cited by examiner

*Primary Examiner* — Hui Chin
(74) *Attorney, Agent, or Firm* — Lynn B. Morreale

(57) ABSTRACT

The invention relates to an epoxidized composition and a process for producing the same. The epoxidized composition is useful as a plasticizer for thermoplastics such as polyvinyl chloride (PVC) and other polymers. The process includes forming a blend containing one or more fatty acid esters and one or more bio-based oils; and epoxidizing the blend to form the epoxidized composition. This process has several advantages over a process of forming a blend of already epoxidized fatty acid esters and epoxidized bio-based oils.

19 Claims, No Drawings

EPOXIDIZED COMPOSITION AND METHODS FOR MAKING THE SAME

CROSS-REFERENCE TO RELATED APPLICATIONS

This application is a national stage application under 35 U.S.C. §371 of PCT/US2011/46697, filed Aug. 5, 2011, which claims benefit to provisional patent application 61/371,409 filed on Aug. 6, 2010, all of which are hereby incorporated by reference in their entireties.

FIELD OF THE INVENTION

The invention relates to a process for producing a blend of epoxidized esters and epoxidized bio-based oils, that can be used as a plasticizer in thermoplastics such as polyvinyl chloride (PVC) and other vinyl polymers. This epoxidized composition can effectively replace all or a portion of phthalate plasticizers currently in wide use. The process for forming the composition involves first blending one or more esters and one or more bio-based oils, followed by epoxidation of this blend. This process has several advantages over a process of blending the separately epoxidized components, and produces a chemically different and uniform blend.

BACKGROUND OF THE INVENTION

Phthalate plasticizers have long been used to impart pliability to thermoplastics such as polyvinyl chloride (PVC), and other vinyl polymers. The addition of a plasticizer generally causes a reduction in the cohesive intermolecular forces along the polymer chains. The chains can then move more freely relative to one another, and the stiffness of the polymer is reduced. Phthalate plasticizers have been reported by some sources to be a health concern when found in direct contact with bodily fluids. Because they are readily miscible in organic solvents like plasma and saliva, humans have a chance of ingesting or absorbing them during common medical procedures.

There is a need for effective plasticizers for thermoplastics and other polymers, that are not based on or contain phthalate plasticizers.

Blends of epoxidized soybean oil have long been used as a part of a plasticizer blend. U.S. Pat. No. 3,639,318 describes a PVC film plasticized with a blend of di-(2-ethylhexyladipate and epoxidized soybean oil.

U.S. Pat. No. 5,227,417 describes using a blend of phosphate ester based plasticizer, brominated aromatic ester plasticizer, and epoxidized soybean oil.

WO 2010/006101 describes the use of epoxidized methyl soyate as a PVC plasticizer. WO 2009102877 describes a blend of soy methyl ester epoxide blended with epoxidized soybean oil. This blend involves the mixture of components previously epoxidized.

Surprisingly, it has now been found that a plasticizing composition may be formed for thermoplastics and other polymers, by a process that includes forming a blend of one or more fatty acid esters and one or more bio-based oils, then epoxidizing the resulting blend. The resulting epoxidized composition is lower in residual contaminants and detrimental reaction by-products, than a blend made by blending together components that had already been epoxidized separately. Additionally, there are many process advantages of using the process of the invention.

SUMMARY OF THE INVENTION

The invention relates to an epoxidized composition comprising;

a) one or more epoxidized fatty acid esters; and
b) one or more epoxidized bio-based oils, where the blend containing a) and b) is free of sodium, calcium and/or magnesium ions, and/or is also free of hydroxy acetate. In some embodiments, the composition is free of sodium, calcium and magnesium ions, and is also free of hydroxy acetate. By "free of" it is meant the composition contains zero or substantially zero of the applicable component(s).

The invention further relates to an epoxidized composition formed by a process including the steps of forming a blend containing one or more fatty acid esters and one or more bio-based oils; and epoxidizing the blend to form an epoxidized composition.

The invention further relates to a plasticized polymer composition that includes one or more polymers (such as in the form of a polymer matrix) and at least one plasticizer, where the plasticizer is homogeneously dispersed therein, the plasticizer being an epoxidized composition as described herein.

DETAILED DESCRIPTION OF THE INVENTION

The invention relates to epoxidized compositions that are useful as plasticizers in thermoplastics and other polymers. The epoxidized composition is formed by a process of forming a blend containing one or more fatty acid esters and one or more bio-based oils, then epoxidizing the resulting blend to form an epoxidized composition. The resultant epoxidized composition can be substituted for all or a portion of phthalate plasticizers in PVC and other polymer containing formulations.

Fatty Acid Esters

The fatty acid esters useful in the invention may be $C_6$ to $C_{22}$ aryl, $C_4$ to $C_{22}$ cycloalkyl, $C_5$ to $C_{22}$ heteroaryl, or $C_{10}$ to $C_{22}$ alkyl fatty acid esters, or mixtures thereof, that are capable of being epoxidized. For example, in some embodiments, esters of fatty acids having at least one point of unsaturation (such as a double bond) in the fatty acid portion of the carbon chain may be used.

Esters of long chain fatty acids (e.g., $C_{10}$ to $C_{22}$ fatty acids or mixtures thereof) such as those derived (e.g., hydrolyzed) from vegetable oils (e.g., olive oil, peanut oil, corn oil, cottonseed oil, soybean oil, linseed oil, sunflower oil, canola oil, and/or coconut oil) or animal fats (e.g., lard or beef tallow) or mixtures thereof are used in some embodiments of the invention. Examples of such long chain fatty acid esters include $C_1$ to $C_{14}$ mono-alkyl esters of $C_{10}$ to $C_{22}$ fatty acids derived from vegetable oils. Useful mono-alkyl esters of fatty acids include, but are not limited to, methyl, ethyl, propyl, butyl, 2-ethylhexyl or octyl esters of $C_{10}$ to $C_{22}$ fatty acids and mixtures thereof. Examples include $C_1$ to $C_{14}$ alkyl esters of oleic acid such as octyl oleate, hexyl oleate, butyl oleate, methyl oleate or mixtures thereof. In some embodiments, fatty acid esters derived from soybean oil are used such as $C_1$ to $C_{14}$ alkyl soyates, especially $C_1$ to $C_8$ alkyl soyates or mixtures thereof. $C_1$ to $C_{14}$ alkyl esters of linoleic acid and linolenic acid or mixtures thereof, such as methyl linoleate are also useful in the invention. Other useful fatty acid esters include, but are not limited to, cyclic esters of long chain fatty acids such as cyclohexyl and benzyl esters of fatty acids derived from vegetable oil. Soy methyl ester (also know as methyl soyate) is especially preferred.

The fatty acid esters are made by means generally known in the art. In one embodiment, soybean oil is transesterfied with a $C_1$ to $C_{14}$ alcohol such as methanol, ethanol, 2-ethyl hexyl alcohol or any other alcohol to make an alkyl ester. In another embodiment, a glycidyl ester of the fatty acid can be prepared using, for example, epichlorohydrin.

Bio-Based Oils

The bio-based oils useful in the invention can be vegetable oils or animal fats or mixtures thereof. Vegetable oils useful in the blend of the invention include olive oil, peanut oil, cottonseed oil, soybean oil, linseed oil, sunflower oil, canola oil, corn oil or mixtures thereof. Animal fats useful in the invention include, but are not limited to lard, beef tallow or components of such animal fats or mixtures thereof. In some embodiments, animal fats are selected that contain esters of oleic acid.

Blend Process

The ratio of fatty acid esters to bio-based oils can be between 90:10 to 10:90 by weight, preferably between 75:25 and 25:75, and more preferably between 60:40 and 40:60. In one embodiment, a weight ratio of about 50:50 between the components is used.

The fatty acid ester(s) and bio-based oil(s) can be blended together by means known in the art. The blending can occur at any time before the epoxidation reaction, but is conveniently done just prior to epoxidation, and in the reaction vessel in which epoxidation will occur. In one embodiment the two oils are metered into a reactor in the selected weight ratio, and admixed with heating to the reaction temperature of 60-80° C. to form a homogeneous admixture. Since the fatty acid ester(s) and bio-based oil(s) are blended before and during the epoxidation reaction, the resulting composition is well homogenized, even for reactants of different weights and viscosities.

Epoxidation

Epoxidation of the homogeneous blend can occur by any method known in the art. In one embodiment, the desired ratio of one or more fatty acid esters and one or more bio-based oils are admixed to form a blend. Other additives, such as solvents, and additives to enhance the epoxidation reaction may be added to the blend prior to or during epoxidation. The blend is heated to the desired temperature for epoxidation (60-80° C.) and reactants are fed/added to the blend to carry out the epoxidation.

In one embodiment, a solvent such as toluene or xylene may optionally be added to the blend of fatty acid esters and bio-based oils to aid the quality of the final epoxide and to ease the processing. An organic acid such as formic, acetic or propionic acid is added to the blend. An inorganic acid such as sulfuric acid may also be optionally added to the blend in order to increase the epoxidation rate. The blend is heated to the desired temperature and then $H_2O_2$ is slowly added to the blend. The reaction is exothermic and must be controlled by cooling and by regulating the addition rate of $H_2O_2$. Measuring the iodine value of the oil can be used to monitor the progress of the reaction. When the desired epoxidation level is achieved, the aqueous phase is separated by gravity and the oil phase is washed to remove any residue of hydrogen peroxide and acid. This oil phase is then stripped under vacuum to remove the moisture, organic acid or any solvents.

In one embodiment, methyl oleate is blended with vegetable oil, such as soybean oil, prior to epoxidation. In other embodiments, the blend contains methyl soyate and a vegetable oil such as soybean oil.

Properties of Product

The process of the invention, and epoxidized composition formed therefrom, yields a different final composition than a composition obtained by merely blending an already epoxidized fatty acid alkyl ester and an epoxidized bio-based oil, such as a vegetable oil. While not being bound by any particular theory, it is believed that the fatty acid alkyl ester and the bio-based oil may interact during the epoxidation process, producing a different reaction product than what would be obtained by mixing the already epoxidized components. The epoxidation of the blend also yields less contaminants relative to a mixture formed by combining the already epoxidized fatty acid esters and bio-based oils.

An advantage of the process of the invention is that in the epoxidation of a blend containing soy methyl ester and vegetable oil, the soy methyl ester acts as a solvent for epoxidation of the vegetable oil. This reduces the need of a separate organic solvent, such as toluene, that must be used to reduce the viscosity of the vegetable oil as it is converted to the epoxide and permits subsequent phase separation and washing. The use of less organic solvent provides a safer, greener process (less organic solvent waste), and a product with less contamination. The elimination of the solvent also creates a more economical process requiring fewer steps, improving throughput, and reducing side reactions in separate epoxidation processes.

The epoxidized composition of the present invention may also be free of traces of alkaline metals (e.g., Na, Ca, and/or Mg ions) found in commercial epoxides, since the use of soy methyl ester in the blend enables one to wash the final epoxide with water, rather than the alkaline salts used to remove traces of acids in a commercial process. Additionally, the composition of the present invention can be free of hydroxyl acetate by-products, such as hydroxy acetate, found in blends of the separately epoxidized blend components.

Further, no centrifuge is needed for liquor separation, as in separate epoxidation processes. The phases can be separated by gravity, and water washing can reduce the residual peroxide. Centrifugation is a significant portion of the capital expense in a process, and its elimination saves overhead cost.

Additionally, the process of the invention reduces the need to filter the composition, saving time and costs associated with the disposal of filter cakes.

Another advantage of the process of the invention over a process in which the components are epoxidized first and then blended, relates to the homogenization achieved in the resultant epoxidized composition. Due to the extended period of agitation during the epoxidation reaction (generally at least 3 hours, and often 6 to 12 hours), the final epoxidized composition is fully homogenized. A blending process of two different epoxidized components may not result in complete homogenization. The presence in a post-epoxidation blend process of epoxidized components having two different viscosities increases the probability of the blend being less than homogeneous. A fully homogenized epoxidized composition is a key actor in successful plasticization of PVC or other polymers.

Uses

The epoxidized composition of the invention is a "bio-plasticizer"—"greener" and is more environmentally friendly than the phthalates that it can substitute for. The epoxidized composition is useful for plasticizing thermoplastics or other polymers such as halogenated polymers, including PVC homopolymers, PVC copolymers, and polyvinyl dichlorides and mixtures thereof. Useful co-monomers with vinyl chloride include, but are not limited to, vinyl acetate, vinyl alcohol, vinyl acetals, vinyl ethers, vinylidene chloride, lower alkyl(meth)acrylates, (meth)acrylic acid, lower alkyl olefins, vinyl aromatics such as styrene and styrene derivatives and vinyl esters and mixtures thereof. Chlorinated polyolefins, chlorinated rubbers, and/or acrylic acid functionalized polymers may also be plasticized using the epoxidized composition of the invention. The epoxidized composition may be used to soften other polymers, including but not limited to polyurethanes, polystyrene and its copolymers, polybutadiene copolymers, polyamides, rubber and/or synthetic rubbers, EPDM (synthetic rubber made from ethylene propylene diene monomer), and other similar polymers. Thermoset polymers may also be plasticized by the epoxidized composition of the invention. In one embodiment, the epoxidized composition is used in biopolymers—such as polylactic acid, polyhydroxy butyrate, or polyamide 11 or mixtures thereof.

The epoxidized composition, in addition to its role as a plasticizer, also acts as an acid scavenger.

The level of epoxidized composition used for plasticizing at least one thermoplastic or other polymer is generally from 1 to 40 wt %, and preferably from 5 to 25 wt %, based on the total weight of the polymers. The epoxidized composition may be used as the sole (primary) plasticizer, or in combination with one or more other plasticizers, such as, but not limited to phthalates, and low and medium molecular weight polymeric plasticizers.

The present invention is also directed to a plasticized polymer composition containing one or more polymers and an epoxidized composition of the present invention where the epoxidized composition is homogenously dispersed in the polymer composition. In some embodiments, the epoxidized composition is used as a plasticizer for the polymers, alone or in combination with other plasticizers. In other embodiments, the polymers in the composition may be in the form of a polymer matrix. The polymer composition may further contain other additives known for use with polymers such as thermoplastics, including, but not limited to fillers, pigments, flame retardants, dyes, stabilizers, UV stabilizers, lubricants, surfactants, flow aids, and/or other plasticizers.

EXAMPLES

Example 1

450 g of soy methyl ester and 450 g of soybean oil were charged to a 2 liter reactor. This mixture was stirred at 400-800 rpm and heated to 60° C. Then 185 grams of 25% formic acid was added to this mixture and 335 g of 70% $H_2O_2$ was slowly added over 4-6 hours. The reaction was monitored by measuring the iodine value of the oil mixture. The reaction lasted 8-12 hours. After reaching the desirable iodine value, the aqueous phase was separated for disposal and the oil phase was given a water wash to remove the residue of peroxide and formic acid. A second water wash could be performed to remove the residue of formic acid and hydrogen peroxide. This oil phase then was steam stripped and dried under full vacuum (less than 6 mm hg). An epoxide with 6.95-7.1% oxirane, iodine value of 1-3, and viscosity of 60-80 cps with a color of less than 100 APHA was obtained. Reaction time can be reduced by introducing a small amount of methane sulfonic acid (MSA) or $H_2SO_4$ (0.5% or less to the reaction mixture).

Example 2

Typical formulations incorporating the epoxidized composition (described as bioplasticizer) are shown in Table 1, based on parts per hundred resin (phr).

|  | cable jacketing | cable insulation | hose and profile |
| --- | --- | --- | --- |
| PVC (K70) | 100 | 100 | 100 |
| bio-plasticizer | 40-60 | 40-60 | 40-60 |

-continued

|  | cable jacketing | cable insulation | hose and profile |
| --- | --- | --- | --- |
| CaCO3 | 20-80 | 20-60 | — |
| lubricant | 0-1 | 0-1 | 0-1 |
| CaZn stabilizer | 3-15 | 3-15 | 0.5-2 |

Such formulations would be expected to retain properties similar to phthalate stabilized formulations in terms of Shore Hardness, Tg, and tensile properties, with, in some instances, improved surface properties.

What is claimed is:

1. An epoxidized plasticizer composition comprising a blend of
    a) one or more unepoxidized fatty acid esters; and
    b) one or more unepoxidized bio-based oil;
    wherein the blend is epoxidized to produce a homogeneous epoxidized plasticizer composition that is phthalate free and free of alkaline metals selected from the group consisting of sodium, calcium and magnesium ions, and is free of hydroxy acetate.

2. The epoxidized composition of claim 1, wherein the unepoxidized fatty acid esters comprise unepoxidized soy methyl ester.

3. The epoxidized composition of claim 1, wherein the unepoxidized bio-based oils comprise unepoxidized soybean oil.

4. The epoxidized composition of claim 1, wherein the unepoxidized fatty acid esters comprise one or more fatty acid esters derived from one or more vegetable oils.

5. The epoxidized composition of claim 4, wherein the unepoxidized fatty acid esters comprise unepoxidized soy methyl ester.

6. The epoxidized composition of claim 4, wherein the composition comprises from 90-10 weight percent of the fatty acid esters, and 10-90 weight percent of the bio-based oils.

7. The epoxidized composition of claim 4, wherein the bio-based oils comprise soybean oil.

8. An epoxidized composition formed by a process comprising the steps of:
    a) forming a blend comprising one or more unepoxidized fatty acid esters and one or more unepoxidized bio-based oils; and
    b) epoxidizing the blend to form an epoxidized composition.

9. The epoxidized composition of claim 8, wherein the blend is free of at least one alkaline metal selected from sodium, calcium or magnesium ions, and is free of hydroxy acetate.

10. The epoxidized composition of claim 8, wherein the unepoxidized fatty acid esters comprise one or more fatty acid esters derived from one or more vegetable oils.

11. The epoxidized composition of claim 10, wherein the unepoxidized fatty acid esters comprise soy methyl ester.

12. The epoxidized composition of claim 8, wherein the blend comprises from 90-10 weight percent of the fatty acid esters, and 10-90 weight percent of the bio-based oils.

13. The epoxidized composition of claim 8, wherein the bio-based oils comprise soybean oil.

14. The epoxidized composition of claim 8, wherein the one or more fatty acid esters act as a solvent for the one or more bio-based oils during the epoxidation step.

15. A plasticized polymer composition comprising one or more polymers and at least one plasticizer homogeneously dispersed within the polymer composition, wherein the plasticizer comprises the epoxidized composition of claim 1.

16. The plasticized polymer composition of claim 15, wherein the polymers comprise one or more homopolymers or copolymers of polyvinyl chloride (PVC).

17. The plasticized polymer composition of claim 15, wherein the polymers comprise one or more bio-polymers selected from polylactic acid, polyhydroxy butyrate, polyamide 11 or mixtures thereof.

18. The plasticized polymer composition of claim 15, wherein the plasticizer is present in the polymer composition in an amount of from 1 weight percent to 40 weight percent, based on the total amount of polymer.

19. The plasticized polymer composition of claim 15, further comprising one or more adjuvants selected from one or more fillers, pigments, flame retardants, dyes, stabilizers, UV stabilizers, lubricants, surfactants, flow aids, plasticizers or combinations thereof.

* * * * *